United States Patent [19]

Ray

[11] Patent Number: 4,591,605

[45] Date of Patent: May 27, 1986

[54] METHOD AND INGESTIBLE FORMULATION FOR INHIBITING THE SECRETION OF STOMACH ACID

[75] Inventor: Tushar K. Ray, Dewitt, N.Y.

[73] Assignee: Research Foundation of State University of New York, Albany, N.Y.

[21] Appl. No.: 437,847

[22] Filed: Oct. 29, 1982

Related U.S. Application Data

[63] Continuation-in-part of Ser. No. 319,929, Nov. 10, 1981, abandoned.

[51] Int. Cl.$^4$ .............................................. A61K 31/13
[52] U.S. Cl. .................................................... 514/579
[58] Field of Search ........................ 424/325; 514/579

[56] References Cited

PUBLICATIONS

Goodman et al., The Pharmacological Basis of Therapeutics, p. 1001 1965.
Melamed et al., GI Pharm. of Polyethyleneimine, J. Pharm. Sci., 66: 899–901 1977.
Belair et al., Effects of Spermine and Spermidine on Gastric Emptying in Rats, J. Pharm. Sci.: 70: 347, 1981.
Ray et al., Polyamines are Inhibitors of Gastric Secretion PNAS 79: 1448–1452 1982.
Remington's Practice of Pharmacy, pp. 450–452 1948.

Primary Examiner—Albert T. Meyers
Assistant Examiner—John W. Rollins, Jr.
Attorney, Agent, or Firm—Charles S. McGuire

[57] ABSTRACT

A method for inhibiting the secretion of stomach acid in vertebrate animals. The method comprises contacting the lumen side of the stomach with a compound which interferes with the acid secretion mechanism yet cannot permeate the lining of the stomach. The compound has a molecular weight of less than 1,200 and at least ten percent of the molecular weight of the compound is due to the molecular weight contribution of secondary amine nitrogen. The invention also includes an ingestible product for inhibiting the secretion of stomach acid in vertebrate animals. The product is ingested so that it is contacted with the lumen side of the stomach to interfere with the acid secretion mechanism without permeating the lining of the stomach. The product contains a compound which has a molecular weight of less than 1200, at least ten percent of the molecular weight of the compound being due to the molecular weight contribution of secondary amine nitrogen. The product is in the form of a solution, dispersion, capsule or tablet.

7 Claims, No Drawings

METHOD AND INGESTIBLE FORMULATION FOR INHIBITING THE SECRETION OF STOMACH ACID

This is a continuation-in-part of copending Patent Application Ser. No. 319,929, filed Nov. 10, 1981, now abandoned.

BACKGROUND OF THE INVENTION

A. Field of the Invention

This invention relates to the inhibition of the secretion of stomach acid in vertebrate animals and more particularly relates to inhibiting or slowing secretion of stomach acid by treating the animal, including human beings, with a chemical compound.

B. History of the Prior Art

The secretion of excess stomach acid has been associated with peptic ulcers, i.e., an ulcer occurring in the lower end of the esophagus, in the stomach, or in the duodenum. Furthermore, excess stomach acid has also been associated with heartburn and other stomach pains.

There have, therefore, been historic attempts to relieve excess stomach acid. Until recently, the effects of excess acid were relieved, with some success, through neutralization, diet and behavioral or emotional modification. The most common method for relieving excess stomach excess was by neutralization. Well known stomach acid neutralizers are, for example, sodium bicarbonate, magnesium hydroxide, calcium carbonate, aluminum hydroxide, aluminum phosphate, magnesium trisilicate, tribasic calcium phosphate, sodium carboxymethylcellulose, dihyroxyaluminum acetate, aluminum carbonate, and calcium tartrate. Certain polyamine methylene resins have also been tried.

Until recently, attempts were also made to inhibit the flow of gastric acid. Compounds which had been tried for this purpose were atropine sulfate and other atropine derivatives. These compounds were not uniformly effective and, in addition, created serious side effects including inhibition of the parasympathetic nervous system, dryness of the mouth, blurring of vision, heart palpitations and toxic psychosis.

Numerous other compounds for inhibiting acid secretion were tried but until recently, none of the compounds excelled in the combination of lowering the output of acid while at the same time, resulting in minimal side effects.

Recently, a compound has been introduced which has been found to be superior in reducing the flow of stomach acid. This compound, commonly known as cimetidine, has the imperical formula $C_{10}H_{16}N_6S$ and has Chemical Abstracts Registration No. 51481-61-9. The compound has some structural similarity to histamine since similar to histamine, it has a heterocyclic imidazole ring. It is believed that the compound functions by entering the blood stream and interferes with histamine receptor sites on the nutrient side of the stomach wall (the side opposite the food containing or lumen side of the stomach wall). It is believed that cimetidine is effective in stopping the secretion of stomach acid by blocking the histamine sites since histamine is believed to be responsible for initiating the flow of stomach acid.

Unfortunately, while being effective in stopping acid flow, cimetidine has been found to have some undesirable characteristics. In particular, use of the cimetidine drug has been found to sometimes impair kidney function and cause mental confusion. There is also some evidence that after use of the drug is discontinued, acid rebound (secretion of acid at a higher than normal rate) can occur. There is furthermore some evidence that cimetidine can inhibit sperm production in adult males using the compound.

BRIEF DESCRIPTION OF THE INVENTION

In accordance with the invention, there is provided a method for inhibiting the secretion of stomach acid in vertebrate animals. The method comprises contacting the lumen side of the stomach with a compound which interferes with the acid secretion mechanism yet cannot permeate the lining of the stomach. The compound has a molecular weight of less than 1,200 and at least 10 percent of the molecular weight of the compound is due to the molecular weight contribution of secondary amine nitrogens. The compound may be a cyclic compound.

Since the compound cannot permeate the stomach lining, based upon knowledge of membrane structure, it is likely the compound would be unable to permeate the other linings in the digestive tract. Side effects from the compound would therefore be minimized when compared with compounds of the prior art which could permeate the stomach and other linings of the digestive tract and were used in an attempt to inhibit the secretion of stomach acid. Such prior art compounds entered the circulatory system of the animal and thus were able to interact with the internal biochemical mechanisms of the animal.

DETAILED DESCRIPTION OF THE INVENTION

As previously discussed, the method of the invention is a method for inhibiting the secretion of stomach acid in vertebrate animals. The invention has been found to be effective upon cold and warm blooded animals which would include human beings based upon the correlation between the secretion mechanisms of the animals tested and human beings.

The biochemical mechanism governing secretion of stomach acid, until recently, has been poorly understood. It has, however, been recognized that hydrogen ions were somehow transported through the lumen side of the stomach wall into the stomach cavity to create the acidic condition. It has been more recently postulated that the flow of hydrogen ions into the stomach cavity across the lumen side of the stomach wall, is accomplished in exchange for potassium ions. It is believed that there are binding sites for potassium on the acid secreting cells in the stomach wall which accept the potassium ion and exchange it for hydrogen ion while transporting the potassium ion to the internal portion of the cell.

While not wishing to be bound by any particular theory, it is believed that the method of the present invention functions by interfering with the potassium binding site, thereby inhibiting hydrogen ion transport into the stomach cavity. It is possible, though not known, that other existing compounds may have previously inhibited the flow of stomach acid by a similar mechanism. Compounds, which may have had this effect, are thiocyanates, $OCN^-$ and $NO_2^-$. $NH_4^+$ another inhibitor of gastric HCl acid secretion is thought to enter into the cell after dissociation into free $NH_3$, which in turn neutralizes the $H^+$ produced at the cellular site. The other inhibitors like substituted benzimidazoles and para chloromecuribenzene sulfonic acid appear to work by inhibiting the pumping mechanism for H+ located at the apical membrane of the acid secreting cells. Unfortunately, all of these compounds either pass through the stomach wall to cause toxicological effects or are otherwise sufficiently inefficient or hazardous to make their use undesirable.

H or lower alkyl of 1 through 6 carbon atoms but is usually H.

Examples of compounds suitable for use in accordance with the present invention are:

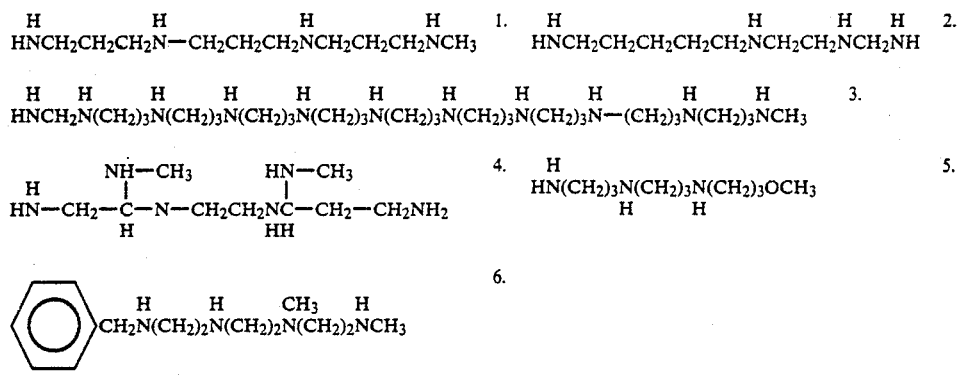

In general, the lumen side of the stomach is contacted with the compound, used in accordance with the present invention, simply by ingesting the compound. The compound, used in accordance with the present method, has a molecular weight of less than 1,200 and usually less than 500. At least 10 percent of the molecular weight of the compound is due to the molecular weight contribution of secondary amine nitrogens.

The compound may contain essentially any chemical groups in addition to secondary amine groups provided that the other chemical groups do not substantially decrease the effectiveness of the compound in inhibiting the secretion of stomach acid, do not substantially increase the tendency of the compound to pass through the wall of the digestive tract, do not cause the compound to irritate the lining of the digestive tract, and do not increase the ratio of the toxicity of the compound to its effectiveness. "Toxicity", as used herein, means long range as well as short range adverse effects upon the organism including carcinogenicity. Groups which usually may be present, in addition to secondary amine groups, are alkyl groups, primary amine groups, tertiary amine groups, phenyl groups, alkoxy groups and hydroxy groups.

The compound is usually a compound of the formula:

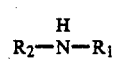

wherein $R_2$ and $R_1$ are independently at each occurrence H, lower alkyl of 1 through 3 carbon atoms or

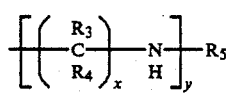

where $R_3$ and $R_4$ are independently at each occurrence H, lower alkyl of 1 through 3 carbon atoms, or an amino group. $R_3$ and $R_4$ are usually H. x is independently at each occurrence an integer of 1 through 5 and is usually an integer of 3 or 4. y is independently at each occurrence an integer of 1 through 10 but is usually an integer of 2 through 4. $R_5$ is independently at each occurrence Particularly suitable compounds for use in accordance with the method of the present invention are spermine, $H_2N(CH_2)_3NH(CH_2)_4NH(CH_2)_3NH_2$, and spermidine, $H_2N(CH_2)_3\text{-}NH(CH_2)_4NH_2$. These compounds, especially spermine, are particularly desirable due to their dramatic effect upon the inhibition of the secretion of stomach acid and because they cannot permeate the stomach lining and are believed unable to permeate the lining of the entire digestive tract. "Cannot permeate", as used herein, means that at least 95 percent of the compound passes through the stomach or digestive tract unaltered or else is chemically converted into non-toxic biologically recognizable compounds before permeating the lining of the stomach or digestive tract.

Spermine and spermidine are further desirable since the unaltered compounds are themselves biologically recognized since they exist naturally in animal tissue and can be either metabolized in accordance with known metabolic paths or can be eliminated in the urine. A discussion of the metabolic fate of spermine and spermidine can be found in "Polyamine Metabolites and Conjugates in Man and Higher Animals: A Review of the Literature", *Physiological Chemistry and Physics* (1980) Volume 12, pages 389-399.

In accordance with the method of the invention, it has been found that the secretion of stomach acid in vertebrate animals can be effectively inhibited when the lumen side of the stomach is contacted with a concentration of the compound of from about 0.1 to about 12 millimolar in the fluid of the stomach (usually equivalent to an ingested dosage of from about 0.05 to about 15 milligrams of the compound per kilogram of body weight of the animal). The preferred concentration of the compound with which the lumen side of the stomach is contacted is usually from about 0.5 to about 10 millimolar for warm blooded animals (usually equivalent to an ingested dosage of from about 1 to about 10 milligrams of the compound per kilogram of body weight of the animal). The most preferred dosage for the greatest inhibition of the secretion of stomach acid at the lowest dosage is believed to be an ingested dose of from about 3 to about 7 milligrams of the compound per kilogram of body weight of the animal. Dosage as low as 0.25 milligrams per kilogram may, however, have some effect. Dosages ingested by the animal may be either predissolved in a fluid or may dissolve in the stomach to contact the lumen side of the stomach wall.

The acid secretion inhibiting effects of the method of the invention can be rapidly reversed in most cases simply by ingestion of sufficient potassium ion which seems to displace the compounds described from interference with the potassium binding site. In the absence of reversal by ingestion of potassium ion, the inhibiting effects usually cease in a matter of hours.

EXAMPLE I

This experiment was carried out with gastric mucosa from bullfrogs (Rana catesbeiana). After the frogs had been pithed, fundic mucosae were carefully separated from the submucosae and mounted over one end of a plastic tube (13×100 mm) with the mucosal surface facing out. The area of the mounted mucosae was 1.5 cm$^2$. The bathing solutions were bubbled continuously with 90% $O_2$-5% $CO_2$.

The normal nutrient solution had the following composition (in mM): NaCl 87, KCl 4, $CaCl_2$ 2, $MgCl_2$ 1, $KH_2PO_4$ 1, $NaHCO_3$ 18, and glucose 11. The secretory solution was 104 mM NaCl.

All experiments were conducted under open-circuit conditions at room temperature. The mucosal solutions were collected at 15-minute intervals and placed in thoroughly washed plastic vials. The K$^+$ content of the secretory medium was determined by atomic absorption spectrophotometer (model 360 Perkin-Elmer). The H$^+$ secretion was quantitated by titration using 1 mM NaOH to pH 6.5 while gassing with 100% $N_2$.

Addition of polyamines to either the nutrient or the secretory solution of a histamine stimulated bullfrog gastric mucosa show different effects on H$^+$ transport. Thus, spermine at 0.5 and 1.0 mM concentrations did not have any appreciable effect from the nutrient side. However, when added into the secretory solution (comparable to the lumen side of the stomach) spermine showed a remarkable inhibition of H$^+$ transport at a concentration 0.25 mM and the inhibition steadily increased with increasing concentrations of spermine. The inhibition of H$^+$ transport by secretory spermine was completely reversible by elevation of K$^+$, which was substituted for Na$^+$ of the secretory solution.

Similar to spermine, spermidine also inhibits gastric H$^+$ transport when added into the secretory solution but not into the nutrient solution. However, the inhibitory effects of spermidine is much lower than spermine. It should be noted that like spermine, the spermidine effects could also be reversed by elevation of secretory K$^+$. The comparative effects of different polyamines on the steady-state level of H$^+$ transport by histamine-stimulated gastric mucosa is shown in Table 1. The diamines (primary amines) at 0.5 mM are totally ineffective in inhibiting gastric acid secretion.

The presence of K$^+$ in either the nutrient or secretory bathing medium of the chambered mucosa is absolutely necessary for gastric acid secretion. When the mucosa is maintained in a K$^+$ free medium for 2-3 hours, the histamine-stimulated acid secretion becomes insignificant, which is elevated by two fold after incorporation of 10 mM K$^+$ into the secretory solution. However, the presence of 1 mM spermine together with 10 mM K$^+$ in the secretory solution reduces the rate of H$^+$ transport to near zero within 30 min. This inhibitory effect of spermine could be reversed by an elevation of the secretory K$^+$; thus demonstrating an antagonism between K$^+$ and spermine at or near the secretory membrane for some step leading to gastric H$^+$ transport.

EXAMPLE 2

Fresh pig stomachs were purchased from a local slaughter house. The gastric microsomal membranes were harvested. All procedures were carried out at 0°-4° C. Briefly, the fundic mucosa from the pig was desquamated and scraped to collect the oxyntic cell-enriched fractions. The mucosal scraping was homogenized gently in a medium consisting of 250 mM sucrose, 0.2 mM EDTA, and 0.2 mM Pipes buffer (pH 6.8) using a loose pestle homogenizer. The homogenate was centrifuged at 8000 g for 5 min. The process was repeated three times. All the supernatants were pooled together and layered over 40 ml of 37% sucrose in 84-ml capacity screw cap tubes and centrifuged at 100,000 g for 5 hours. The microsomal membrane bands appeared at the interface of soluble supernatant and 37% sucrose. The microsomal vesicle bands were collected, diluted with homogenizing medium, and centrifuged at 100,000 g for 90 min. The pellet was suspended in the homogenizing medium with a protein concentration of 0.5 mg/ml. The collected cellular vesicles were inverted, i.e., the interior of the vesicles originally faced the lumen side of the stomach.

Vesicular accumulation of H$^+$ was measured at room temperature. The method uses the change in fluorescence intensity (quenching) of 9-amino-acridine or acridine orange which is proportional to the amount of dye taken up by the microsomes. The amount of dye taken up is a sensitive measure of intravesicular H$^+$ concentration. Wavelengths used were 493→530 nm (excitation→emission) for acridine orange in a spectrofluorometer. Gastric microsomal vesicles derived primarily from the apical and tubulovesicular membranes of the parietal cells are highly enriched in (H$^+$+K$^+$)-ATPase which has recently been identified as the enzymatic mechanism for the transport of H$^+$ in exchange for K$^+$. The data show the effects of spermine on vesicular H$^+$ uptake mediated by the gastric (H$^+$+K$^+$)-ATPase system. As previously mentioned, K$^+$ is necessary for gastric acid secretion, therefore, the vesicles are preequillibrated in 150 mM KCl with and without 0.5 mM spermine at 0.4° C. for 48 hours. The H$^+$ uptake by the vesicles containing spermine is totally obliterated.

These examples indicate that secondary polyamines (i.e., spermine and spermidine) are effective inhibitors of gastric acid secretion by histamine-stimulated bullfrog gastric mucosa and by pig gastric microsomal vesicles; spermine being more potent than spermidine. The primary diamines are virtually ineffective at comparable dose levels (Table 1). The data also demonstrates that the anti-secretory effects of secondary polyamines are only manifested from the luminal side of the chambered mucosa, suggesting that the highly charged polyamines are relatively impermeable to the acid secreting cells and the effects are exerted at the secretory membrane accessible from the luminal side.

TABLE 1

Effects of spermine, spermidine, putrescine and propanediamine on histamine stimulated steady-state H$^+$ secretory rate.

| Concentration of drug (mM) in the secretory solution | Rate of H$^+$ transport (% of control) | Number of Experiments |
| --- | --- | --- |
| None (control) | 100 | 10 |
| Spermine (0.5) | 28 ± 6 | 6 |
| Spermidine (0.5) | 55 ± 2 | 6 |
| Putrescine (0.5) | 95 ± 10 | 3 |

TABLE 1-continued

Effects of spermine, spermidine, putrescine and propanediamine on histamine stimulated steady-state H+ secretory rate.

| Concentration of drug (mM) in the secretory solution | Rate of H+ transport (% of control) | Number of Experiments |
|---|---|---|
| Propanediamine (0.5) | 92 ± 8 | 3 |

The H+ secretory rates are the steady-stage values before (None) and after addition of the drugs attained by the histamine stimulated mucosa. Values are mean ±SEM.

The compounds used in accordance with the present invention, i.e. secondary amine compounds having a molecular weight below 1200 which interfere with the stomach acid secretion mechanism without permeating the stomach lining, can be administered in solution, in suspension, in capsules or in tablets, and such ingestible solutions, suspensions, capsules and tablets form a part of the present invention. More particularly, the invention includes ingestible suspensions and solutions which contain from about 50 to about 500 milligrams per teaspoon of such a secondary amine compound.

"A secondary amine compound" as used herein is intended to include mixtures of one or more such compounds and effective inorganic and organic salts thereof. An example of such a salt which has been found suitable is spermine tetrahydrochloride. Other such salts are spermine phosphate, spermine sulfate and spermine acetate.

The most common carrier in such solutions is water, although other polar solvents such as alcohol may be used. Nonpolar solvents such as mineral oil may be used as the carrier in a suspension and under certain circumstances, when the compound is a water insoluble salt, water may be used as the carrier in a suspension.

Ingestible tablets and capsules in accordance with the present invention similarly each contain from about 50 to about 500 milligrams of such a secondary amine compound. Such capsules and tablets are prepared in accordance with methods well known to those skilled in the art. "Ingestible" as used herein means of sufficiently low toxicity to permit reasonably safe oral administration and of suitable palatability and pH for such oral administration. The active ingredient is combined with any suitable inert binder of the type commonly used in preparing solid tablets and capsules for oral ingestion to provide a product of desired size and weight. The dosage, in whatever form administered, would be taken, of course, prior to ingestion of food by individuals susceptible to excess stomach acid secretion, e.g., 10 to 20 minutes before mealtime.

What is claimed is:

1. An ingestible suspension containing from about 50 to about 500 milligrams per teaspoon of a compound selected from the group consisting of spermine and derivatives thereof and having a molecular weight below 1200, at least 10% of the molecular weight of the compound being due to the molecular weight contribution of secondary amine nitrogen, which interferes with the stomach acid secretion mechanism without permeating the stomach lining.

2. An ingestible solution containing from about 50 to about 500 milligrams per teaspoon of a compound selected from the group consisting of spermine and derivatives thereof and having a molecular weight below 1200, at least 10% of the molecular weight of the compound being due to the molecular weight contribution of secondary amine nitrogen, which interferes with the stomach acid secretion mechanism without permeating the stomach lining.

3. An ingestible capsule containing from about 50 to about 500 milligrams of a compound selected from the group consisting of spermine and derivatives thereof and having a molecular weight below 1200, at least 10% of the molecular weight of the compound being due to the molecular weight contribution of secondary amine nitrogen, which interferes with the stomach acid secretion mechanism without permeating the stomach lining.

4. An ingestible tablet containing from about 50 to about 500 milligrams of a compound selected from the group consisting of spermine and derivatives thereof and having a molecular weight below 1200, at least 10% of the molecular weight of the compound being due to the molecular weight contribution of secondary amine nitrogen, which interferes with the stomach acid secretion mechanism without permeating the stomach lining.

5. A method for inhibiting the secretion of stomach acid in humans comprising orally administering a dosage of from about 0.05 to about 15 milligrams of a compound selected from the group consisting of spermine and derivatives thereof per kilogram of body weight said compound having a molecular weight of less than 1200, at least 10% of the molecular weight of the compound being due to the molecular weight contribution of secondary amine nitrogen, whereby said compound contacts the lumen side of the stomach without penetrating the stomach lining to interfere with the acid secretion mechanism.

6. The method of claim 5 wherein said compound has a molecular weight of less than 200.

7. The method of claim 5 wherein said dosage is from about 1 to about 10 milligrams of the compound per kilogram of body weight.

* * * * *